United States Patent

Totakura

[11] Patent Number: 6,063,105
[45] Date of Patent: May 16, 2000

[54] MEDICAL DEVICES FABRICATED FROM ELASTOMERIC ALPHA-OLEFINS

[75] Inventor: Nagabushanam Totakura, North Haven, Conn.

[73] Assignee: United States Surgical, Norwalk, Conn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/664,404

[22] Filed: Jun. 18, 1996

[51] Int. Cl.[7] .................................................. A61B 17/00
[52] U.S. Cl. .............................................................. 606/228
[58] Field of Search ..................... 606/228, 229, 606/230, 231; 525/323

[56] References Cited

U.S. PATENT DOCUMENTS

| | | | |
|---|---|---|---|
| 3,630,205 | 12/1971 | Listner | 128/335.5 |
| 4,228,263 | 10/1980 | Howard, Jr. et al. | 526/154 |
| 4,335,225 | 6/1982 | Collett et al. | 525/240 |
| 4,520,822 | 6/1985 | Menezes et al. | 128/335.5 |
| 4,557,264 | 12/1985 | Hinsch | 128/335.5 |
| 4,620,542 | 11/1986 | Menezes et al. | 128/335.5 |
| 4,621,638 | 11/1986 | Silvestrini | 128/335.5 |
| 4,911,165 | 3/1990 | Lennard et al. | 606/231 |
| 5,269,807 | 12/1993 | Liu | 606/228 |
| 5,594,080 | 1/1997 | Waymouth et al. | 526/126 |

OTHER PUBLICATIONS

Coates and Waymouth, Oscillating Stereocontrol: A Strategy for the Synthesis of Thermoplastic Elastomeric Polypropylene, Jan. 13, 1995, Science vol. 267.

K. B. Wagener, Oscillating Catalysts: A New Twist for Plastics, Jan 13, 1995, Science vol. 267.

R. Baum, Elastomeri, Polypropylene Oscillating catalyst controls microstructing Jan. 16, 1995, C&E News.

*Primary Examiner*—Michael Buiz
*Assistant Examiner*—Vikki Trinh

[57] ABSTRACT

Medical devices made in whole or in part from homopolymers, copolymers, and/or blends containing thermoplastic elastomeric poly(alpha-olefins), including both monofilament and multifilament sutures, are provided. In particular, such homopolymers, copolymers, and/or blends contain thermoplastic elastomeric polypropylene.

13 Claims, 1 Drawing Sheet

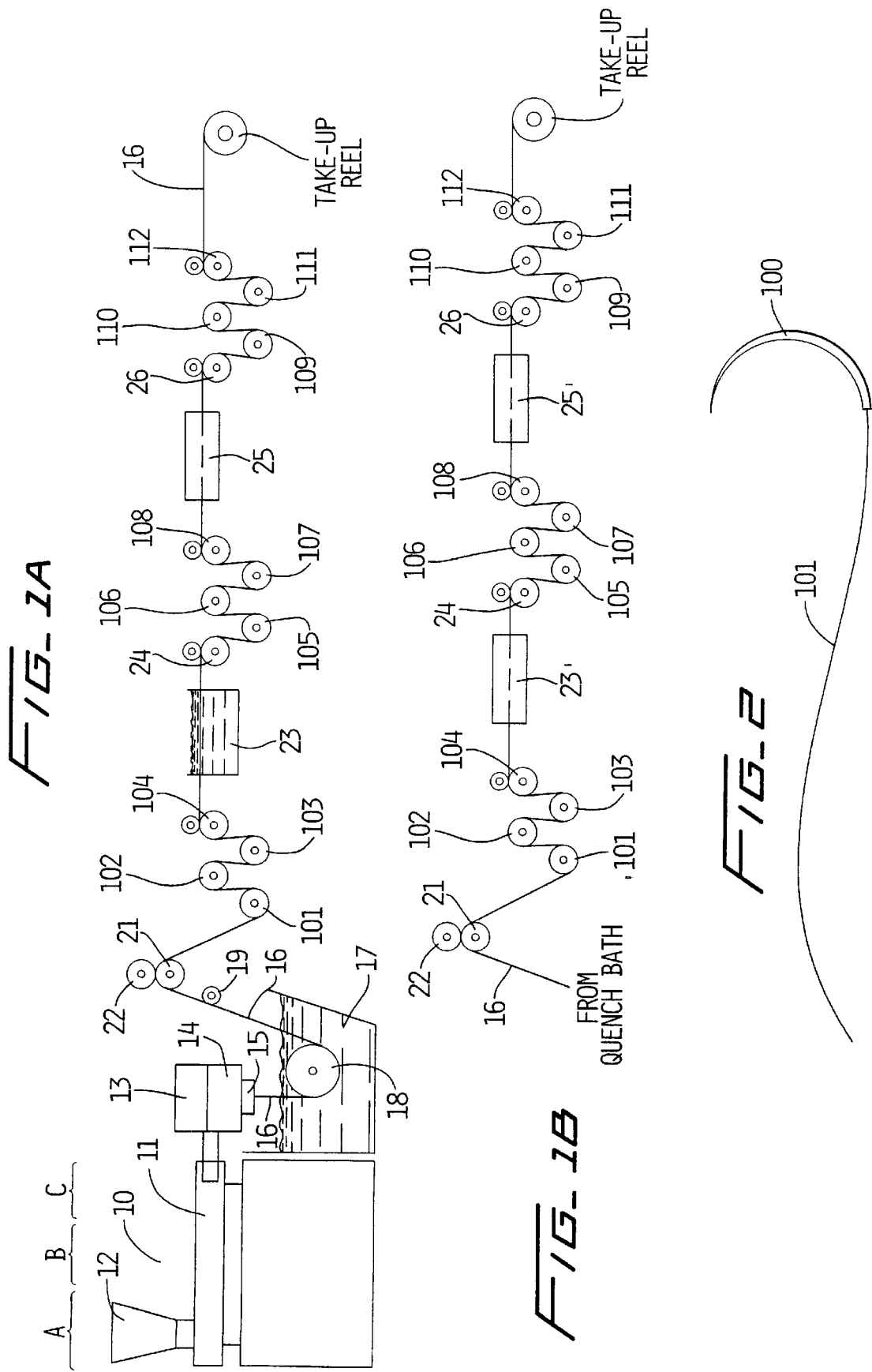

MEDICAL DEVICES FABRICATED FROM ELASTOMERIC ALPHA-OLEFINS

TECHNICAL FIELD

Medical devices made totally or in part from elastomeric poly(alpha-olefins), including both monofilament and multifilament sutures, are provided. In particular, medical devices made totally or in part form elastomeric polypropylene, including both monofilament and multifilament sutures, are provided.

BACKGROUND OF THE INVENTION

Sutures fabricated from polypropylene homopolymers and copolymers are from polymer blends containing polypropylene are disclosed in, among others, U.S. Pat. Nos. 3,630,205, 4,621,638 and 4,911,165 (sutures obtained by the melt extrusion of isotactic polypropylene), U.S. Pat. Nos. 4,520,822 and 4,620,542 (sutures made from ethylene-propylene copolymers) and U.S. Pat. No. 4,557,264 (sutures made from blends of polypropylene and linear low density polyethylene).

Medical devices, including sutures, fabricated from syndiotactic polypropylene and/or a blend of syndiotactic polypropylene and at least one other thermoplastic polymer are disclosed in U.S. Pat. No. 5,269,807.

Atactic isotactic stereoblock alpha-olefin polymers, including polypropylene, are disclosed in *Oscillating Stereocontrol: A Strategy for the Synthesis of Thermoplastic Elastomeric Polypropylene Science,* Coates and Waymouth, Vol. 267, Jan. 13, 1995. Such stereoblock alpha-alpha-olefin polymers are reported therein to be thermoplastic elastomeric alpha-olefins.

As good as commercially available polypropylene sutures are today, it would be advantageous to provide a suture, which exhibits even greater flexibility and handling characteristics then commercially available polypropylene sutures while maintaining other desired characteristics, such as tensile strength, knot strength, and knot retention.

SUMMARY OF THE INVENTION

It has now been found that medical devices such as clips, staples, other fasteners, sutures, pins, screws, prosthetic devices, wound dressings, drug delivery devices, anastomosis rings, and other implantable devices can be fabricated from a thermoplastic elastomeric alpha-olefin.

Fibers may be spun from the thermoplastic elastomeric alpha-olefin. These fibers can be knitted or woven with other fibers, either absorbable or nonabsorbable, to form meshes or fabrics.

In a particularly useful embodiment, the fibers can be fabricated into both monofilament and braided multifilament sutures.

BRIEF DESCRIPTION OF THE DRAWINGS

FIG. 1A is a schematic illustration of an apparatus which is suitable for manufacturing monofilament thermoplastic elastomeric alpha-olefin sutures; and, FIG. 1B is a modification of the apparatus of FIG. 1A which is particularly suitable for manufacturing the monofilament sutures of smaller size, e.g., size 4/0 and smaller.

FIG. 2 is a perspective view of a suture attached to a needle.

DESCRIPTION OF THE PREFERRED EMBODIMENTS

The expression "thermoplastic elastomeric alpha-olefin" as used herein includes alpha-olefin polymers that have segments with isotactic stereocenters connected to segment with attactic centers. This stereoblock polymeric material is disclosed in *Oscillating Stereocontrol; A Strategy for the Synthesis of Thermoplastic Elastomeric Polypropylene Science,* Coates and Waymouth, Science Vol. 267, Jan. 13, 1995 and further described in *Oscillating Catalysts: A New Twist for Plastics,* K. B. Wagener, Science Vol 267, Jan. 13, 1995 the contents of both these articles being incorporated therein by reference.

Random, block, or graft copolymers can be formed from the copolymerization of the thermoplastic elastomeric alpha-olefin, preferably elastomeric polypropylene with one or more monomers or sequences of monomers copolymerizable therewith; which include other alpha-olefins such as ethylene and non-elastomeric polyproylene units e.g. isotactic, syndiotactic and/or atactic.

In addition any of these polymers can be blended with one or more other suitable resins to provide useful moldable or extrudable articles. Blends of the thermoplastic elastomeric alpha-olefin resins with one or more other thermoplastic resin preferably contain from about 5 to about 95 weight percent, and more preferably from about 20 to about 80 weight percent, thermoplastic elastomeric alpha-olefin, the balance of the blend containing, e.g., isotactic polypropylene, Atactic polypropylene, or syndiotactic polypropylene etc. Preferably the thermoplastic elastomeric alpha-olefin is a thermoplastic elastomeric polyproylene.

The thermoplastic elastomeric polymers and blends provided herein can be used in the fabrication in whole or in part of a variety of medical devices. These include, but are not limited to sutures, suture coatings, pins, screws, clips and other fasteners, gauze, wound dressings, hernial repair meshes, vascular grafts (e.g. fabrics and/or tubes) anastomosis rings, prosthetic ligaments and tendons, growth matrices, drug delivery devices and other implantable medical devices.

The polymers or blends herein may be formed into surgical articles using any known technique, such as, extrusion, molding and/or solvent casting. The polymers polymers or blends can be spun into fibers to be used as sutures, either monofilament or multifilament. Additionally, such fibers can be woven with other fibers, either absorbable or nonabsorbable, to form meshes or fabrics.

Multifilament sutures may be made by methods known in the art. Braid constructions such as those disclosed and claimed in U.S. Pat. Nos. 5,059,213 and 5,019,093 are suitable for the multifilament suture.

A suitable process for the manufacture of monofilament sutures of the present invention comprises the operations of melt extruding the resin to provide a monofilament, stretching the solidified monofilament in water (or other suitable liquid medium) or in air (or other suitable gaseous medium) at a stretch to provide a stretched monofilament. Optionally, the monofilament can be annealed to provide a finished suture. It is contemplated that the monofilament may be frozen prior to annealing.

FIG. 1A schematically illustrates a monofilament suture manufacturing operation which is especially suitable for producing larger size sutures, e.g., those of sizes 3/0 and larger. Extruder unit 10 is of a known or conventional type and is equipped with controls for regulating the temperature of barrel 11 in various zones thereof, e.g., progressively higher temperatures in three consecutive zones A, B and C along the length of the barrel. Pellets or powder of resins of the present invention are introduced to the extruder through hopper 12. Any of the block copolymers of the present invention which are useful for the formation of fibers can be used herein.

Motor-driven metering pump 13 delivers melt extruded resin at a constant rate to spin pack 14 and thereafter through spinneret 15 possessing one or more orifices of desired diameter to provide a molten monofilament 16 which then enters quench bath 17, e.g., containing water, where the monofilament solidifies. The distance monofilament 16 travels after emerging from spinneret 15 to the point where it enters quench bath 17, i.e., the air gap, can vary and can advantageously be from about 0.5 to about 100 cm. If desired, a chimney (not shown), or shield, can be provided to isolate monofilament 16 from contact with air currents which might otherwise affect the cooling of the monofilament in an unpredictable manner.

Monofilament 16 is passed through quench bath 17 around driven roller 18 and over idle roller 19. Optionally, a wiper (not shown) may remove excess water from the monofilament as it is removed from quench bathe 17. On exiting the quench bath the monofilament is wrapped around a first godet 21 provided with nip roll 22 to prevent slippage which might otherwise result from the subsequent stretching operation; and subsequently wrapped around godets 101, 102, 103 and 104 or any other suitable godet arrangement. Monofilament 16 passing from godet 104 is stretched, to effect its orientation and thereby increase its tensile strength.

In the stretching operation shown in FIG. 1A, generally suitable for larger size sutures, e.g., sizes 2 to 3/0, monofilament 16 is drawn through hot water (or other suitable liquid medium) draw bath 23 by means of godets 24, 105, 106, 107 and 108 or any other suitable arrangement of godets which rotate at a higher speed than godet 104 to provide the desired stretch ratio.

In the alternative stretching operation shown in FIG. 1B, generally preferred for smaller sutures sizes, e.g., size 4/0 to 8/0, monofilament 16 is drawn by godets 24, 105, 106, 107 and 108 or any other suitable godet arrangement through hot air convection oven chamber 23 to provide the desired amount of stretch. Following the stretching operation shown in FIG. 1A or 1B, monofilament 16 optionally may be subjected to an on-line annealing and/or additional stretching without shrinkage or relaxation with shrinkage operation as a result of which the monofilament shrinks. In the processes of FIGS. 1A and 1B, on line annealing with or without relaxation when desired is accomplished by driving monofilament 16 by godets 26, 109, 110, 111 and 112 or any other suitable godet arrangement through second hot air oven chamber 25. For relaxation, the third godet rotates at a slower speed than the second godet thus relieving tension on the filament.

The thermoplastic elastomeric alpha-olefin suture provided herein, suture 101, may be attached to a surgical needle 100 as shown in FIG. 2 by methods well known in the art. Wounds may be sutured by passing the needled suture through tissue to create wound closure. The needle preferably is then removed from the suture and the suture tied.

It is contemplated that it may be desirable to dye the sutures of the present invention in order to increase visibility of the suture in the surgical field. Dyes known to be suitable for incorporation is sutures can be used. Such dyes include but are not limited to carbon black, bone black, D&C Green No. 6, and D&C Violet No. 2 as described in the handbook of U.S. Colorants for Food, Drugs and Cosmetics by Daniel M. Marrion (1979). Preferably, sutures in accordance with the invention are dyed by adding up to about a few percent and preferably about 0.2% dye, such as D&C Violet No. 2 to the resin prior to extrusion.

What is claimed is:

1. A medical device formed totally or in part from a stereoblock thermoplastic elastomeric alpha-olefin having segments that have isotactic stereo centers connected to segments having atactic stereo-centers.

2. The medical device of claim 1, wherein said suture is a monofilament suture.

3. The medical device of claim 1, wherein said medical device is selected from the group consisting of meshes, wound dressings, gauze, and vascular grafts.

4. The medical device of claim 1, wherein said thermoplastic elastomeric alpha-olefin is a thermoplastic elastomeric polypropylene.

5. The medical device of claim 1, wherein the thermoplastic elastomeric alpha-olefin is present in a blend with at least one other thermoplastic polymer.

6. The medical device of claim 5, wherein the blend contains form about 5 to about 95 weight percent thermoplastic elastomeric alpha-olephin "and from about 95 to about 5 weight percent of the blend containing at least one other thermoplastic polymer.

7. The medical device of claim 6, wherein the blend contains from about 20 to about 80 weight percent thermoplastic elastomeric olephin "and from about 80 to about 20 weight percent of the blend" containing at least one other thermoplastic polymer.

8. The medical device of claim 5, wherein thermoplastic elastomeric alpha-olefin is a thermoplastic elastomeric polypropylene and is present in a blend with a member selected from the group consisting of isotactic polypropylene, attactic polypropylene, syndiotactic polypropylene, and combinations thereof.

9. The medical device of claim 1, wherein the thermoplastic elastomeric alpha-olefin is present in a copolymer with at least one other alpha-olefin.

10. The medical device of claim 9 wherein said other alpha-olefin is selected from the group consisting of isotactic polypropylene units, attactic polypropylene units, syndiotactic polypropylene units and combinations thereof.

11. A medical device comprising a needle suture combination comprising a filament spun from a composition comprising a stereoblock thermoplastic elastomeric polypropylene having segments that have isotactic stereo-centers connected to segments with atactic stereo-centers.

12. The medical device of claim 11, further comprising a filament spun from a composition comprising a blend of the thermoplastic elastomeric polypropylene with a member selected from the group consisting of ethylene, syndiotactic polypropylene units, atactic polypropylene units, and isotactic polypropylene units.

13. A method of suturing a wound comprising:

a) providing a needled suture fabricated from a stereoblock thermoplastic elastomeric polypropylene having isotactic stereo-centers connected to segments with atactic stereo-centers; and b) passing said needled suture through tissue to create wound closure.

* * * * *